US012778848B2

(12) United States Patent
Karavas et al.

(10) Patent No.: US 12,778,848 B2
(45) Date of Patent: Nov. 3, 2026

(54) PROCESS AND APPARATUS FOR PREPARING VISCOUS PHARMACEUTICAL FORMULATIONS

(71) Applicant: PHARMATHEN S.A., Pallini Attikis (GR)

(72) Inventors: Evangelos Karavas, Pallini Attikis (GR); Efthymios Koutris, Pallini Attikis (GR); Sotiria Chaitidou, Pallini Attikis (GR); Aikaterini Kotti, Pallini Attikis (GR); Adamantia Syrigou, Pallini Attikis (GR); Andreas Stefopoulos, Pallini Attikis (GR)

(73) Assignee: PHARMATHEN S.A., Pallini Attikis (GR)

( * ) Notice: Subject to any disclaimer, the term of this patent is extended or adjusted under 35 U.S.C. 154(b) by 941 days.

(21) Appl. No.: 18/040,664

(22) PCT Filed: Aug. 6, 2021

(86) PCT No.: PCT/EP2021/025304
§ 371 (c)(1),
(2) Date: Feb. 6, 2023

(87) PCT Pub. No.: WO2022/028739
PCT Pub. Date: Feb. 10, 2022

(65) Prior Publication Data

US 2023/0277417 A1 Sep. 7, 2023

(30) Foreign Application Priority Data

Aug. 7, 2020 (LU) ........................................ 101974
Aug. 10, 2020 (GR) .............................. 20200100469

(51) Int. Cl.
*A61J 3/00* (2006.01)
*A61K 9/06* (2006.01)
(Continued)

(52) U.S. Cl.
CPC ..................................... *A61J 3/00* (2013.01); *A61K 9/06* (2013.01); *A61K 38/12* (2013.01); *A61K 47/12* (2013.01)

(58) Field of Classification Search
CPC .... A61J 3/00; A61J 1/20; A61J 1/2003; A61J 1/2089; A61M 2039/0027; A61M 5/19;
(Continued)

(56) References Cited

U.S. PATENT DOCUMENTS

2001/0016703 A1* 8/2001 Wironen ............. A61L 27/3604 604/82
2001/0018571 A1* 8/2001 Hughes ............... A61M 5/1409 604/152
(Continued)

FOREIGN PATENT DOCUMENTS

EP 2 523 653 A2 11/2012
EP 2 823 808 A1 1/2015
WO WO 2011/085957 A2 7/2011

OTHER PUBLICATIONS

International Search Report issued on Nov. 12, 2021 in the International Application No. PCT/EP2021/025304 citing references therein, 4 pages.
(Continued)

*Primary Examiner* — Nilay J Shah
(74) *Attorney, Agent, or Firm* — Oblon, McClelland, Maier & Neustadt, L.L.P.

(57) ABSTRACT

A process may allow the preparation of one or more viscous pharmaceutical formulations and an apparatus may be configured for implementing such a process. A gellable material may be introduced into one chamber, a vehicle may be introduced in the other and by alternately applying force to each chamber, mixing and homogenization may take place. The internal diameter of the connection equipment of the two chambers may be equal to the outlet internal diameters of the chambers. Each chamber may have different diameter, with the first chamber being larger than the second chamber, so as to allow the process to be executed in a simple and more convenient manner.

28 Claims, 9 Drawing Sheets

(51) Int. Cl.
*A61K 38/12* (2006.01)
*A61K 47/12* (2006.01)

(58) Field of Classification Search
CPC ............ A61M 5/2448; A61M 5/16827; A61M 5/284; A61M 2039/1083; A61M 2039/1088
See application file for complete search history.

(56) References Cited

U.S. PATENT DOCUMENTS

| | | | | |
|---|---|---|---|---|
| 2006/0253082 | A1* | 11/2006 | McIntosh ................ | A61M 5/19 604/82 |
| 2013/0079282 | A1* | 3/2013 | Montes ..................... | A61P 5/08 514/11.1 |
| 2013/0292004 | A1* | 11/2013 | Ducret .................... | B01F 35/75 141/351 |
| 2016/0151447 | A1 | 6/2016 | Bielsa Guivernau et al. | |
| 2016/0317799 | A1* | 11/2016 | Tohse ............... | A61B 17/12186 |
| 2016/0339075 | A1 | 11/2016 | Montes et al. | |
| 2019/0167754 | A1 | 6/2019 | Montes et al. | |
| 2019/0290690 | A1* | 9/2019 | Von Isenburg .... | A61K 38/1866 |

OTHER PUBLICATIONS

Anon Ous, "Highlights of Prescribing Information These highlights do no include all the information needed to use FENSOLVI safely and Effectively. See full prescribing information for FENSOLVI"; May 31, 2020; XP055788274, Retrieved from the Internet: URL:https://WWW.accessdata.fda.gov/drug; pp. 1-16.

* cited by examiner

PROCESS AND APPARATUS FOR PREPARING VISCOUS PHARMACEUTICAL FORMULATIONS

CROSS-REFERENCE TO RELATED APPLICATIONS

The present application is the national stage of international application PCT/EP2021/025304, filed on Aug. 6, 2021, and claims the benefit of the filing date of Luxembourg Appl. No. 101974, filed on Aug. 7, 2020, and Greek Appl. No. 2020-0100469, filed on Aug. 10, 2020.

TECHNICAL FIELD OF THE INVENTION

The present invention relates to a process for the preparation of viscous pharmaceutical formulations and to an apparatus for implementing the process. In particular, the present invention relates to the manufacturing of viscous pharmaceutical formulations, such as hydrogels, using an apparatus with specific design characteristics.

BACKGROUND OF THE INVENTION

Controlled release dosage forms improve the effectiveness of drug therapy, by enhancing the therapeutic efficacy of a drug and reducing administration frequency while there is less symptomatic exposure through lower plasma levels of the controlled release drug which reduces the intensity of side effects. When those dosage forms are administered by injection, they are defined as injectable controlled release dosage forms.

A well-known category of injectable controlled release dosage forms are depots. For certain drugs that (i) have a broad therapeutic window, (ii) require a low daily dose and (iii) are going to be used for the long-term treatment of disease, injectable controlled release depots such as microparticles, suspensions and semi-solid compositions, may provide an alternative delivery strategy, potentially making an otherwise undeliverable drug deliverable. Depot systems can be used advantageously to protect peptides, proteins and other biologically active substances by stabilizing them from rapid deactivation and thus preserving their pharmacological efficacy and permitting administration in low doses. Additional advantages of depot systems include a reduction in undesired side effects, due to the ability to provide lower doses, reduction in the total number of administrations, and the potential for controlled as well as targeted release of the active agents.

One of the most interesting depots, are gels, particularly hydrogels. Hydrogel formulations provide several advantages in terms of reduced dosing frequency, prolonged drug delivery and reduced side effects. The process of the present invention provides pharmaceutical formulations, forming sustained-release depots within a patient, without the need for any extemporaneous dissolution or pre-treatment of the formulation. Homogeneity is a critical quality attribute of hydrogel dosage forms. Hydrogels are also mentioned in literature as semi-solid forms.

Hydrogels which are additionally biodegradable offer advantageous solutions because using biodegradable systems eliminates the need for the removal of the "ghost" drug delivery system after all the drug is released. The biodegradable hydrogel systems present unique advantages in drug delivery, such as improved biocompatibility and improved flexibility in controlling the stability and diffusion properties of the protein drugs. In addition, drug targeting to a selected region of the body can be achieved using the biodegradable hydrogel systems.

There are four different types of hydrogels formulations: (i) those with well-ordered lamellar structures, some of these are lyotropic liquid-crystalline phases: (ii) those with cross-linked polymeric networks swollen with vehicle (solution), in these phases the polymer chains are disordered; (iii) those with polymer networks in which the chain-chain interactions are physical, the chains may be predominantly disordered, but regions of local order (especially where inter-chain interactions occur) may also exist; and (iv) those with particulate disordered structures, they include materials in which the gel networks are comprised of fibrils.

Hydrogel formulations are an example of viscous pharmaceutical formulations, exhibiting values of viscosity as shown below.

| | Order of magnitude |
|---|---|
| Low viscosity | $10^0$ cP |
| Medium viscosity | Between $10^0$ cP and $10^2$ cP |
| High viscosity | $\geq 10^3$ cP |

Generally, in the preparation of gel and hydrogel formulations, laminar flow shows dominance over turbulent flow, where laminar flow refers to the type of fluid (gas or liquid) flow in which the fluid travels smoothly or in regular paths, in contrast to turbulent flow, in which the fluid undergoes irregular fluctuations and mixing. Adequately designed mixing equipment is needed for efficient mixing of viscous liquids. Briefly, previously paddles, anchor impellers, screw blades, and kneading mixers have been used to enhance mixing and provide a homogeneous final formulation. Two specialized impellers, known as Z blade or sigma blades, are used to promote mixing in the region closer to the wall of a mixing tank along with a narrow clearance between the impeller blades and the wall of the mixing tank to obtain maximum mixing efficiency.

Despite all the modifications made to enhance the mixing of viscous liquids, several problems are evident such as (i) increased temperature due to the mechanical stirring; (ii) difficulties in collecting the final product and subjecting it to a single-dosage filling process (human intervention); (iii) power consumption to the increased power required for the adequate mixing of semi-solid formulations; (iv) difficulties that emerge from the nature of lyophilized powders, typically used in the manufacturing of semi-solid formulations; and (v) problems related to sufficient homogeneity of the viscous mixture which also affect batch-to-batch consistency, a property which is critical particularly for controlled release pharmaceutical products.

Further to the above challenges, the mixing equipment for the preparation of viscous pharmaceutical formulations should be tightly sealed systems with minimum headspace in order to minimize any water loss and/or product mass drying during manufacturing.

SUMMARY OF THE INVENTION

As discussed above, despite all modifications made to enhance the mixing of viscous liquids, there is a need for an improved and straightforward process for manufacturing viscous pharmaceutical formulations with increased homogeneity and consistency and which avoid some or all of the problems stated above.

The present invention provides a robust, reproducible and straightforward manufacturing process for the preparation of viscous pharmaceutical formulations and formulations comprising combining a gellable material with a vehicle by using a two-chamber apparatus wherein one chamber contains the gellable material and the other chamber contains the vehicle and repeatedly moving the contents of one chamber to the other chamber and where the chambers have a specific ratio of internal diameters. The gellable material can be an inactive ingredient or an API with self-assembling properties and inherent gellable properties.

More particularly the apparatus comprises an interconnected two chamber system equipped with means for applying a force to either or both chambers. Applying a force alternately to each chamber provides a reciprocating movement moving the contents of one chamber into the other chamber. The means for applying the force to the contents of the chambers may be pneumatic using a compressed gas, such as compressed air, acting directly on the content of the chamber, or may be achieved by a piston movably positioned within the chamber with a means for applying pressure to the piston to move it longitudinally within the chamber and thereby move the content of one chamber into the other chamber.

The gellable material, e.g. an API with gelling properties, is introduced into one chamber, a vehicle is introduced in the other and by alternately applying force to each chamber, mixing and homogenization takes place. The internal diameter of the connection equipment of the two chambers is equal to the outlet internal diameters of the chambers. And each chamber is chosen to have different diameter, with the first chamber being larger than the second chamber, so as to allow the process to be executed in a simple and more convenient manner, thus overcoming the need for increased power consumption and excess mechanical strength.

The present invention provides a homogeneous viscous pharmaceutical formulation through a process that has one or more of the advantages of: (i) limited number of processing steps; (ii) no stagnant areas present inside the interconnected two chamber system; (iii) power saving operation during homogenization; (iv) facilitating the collection of the final viscous pharmaceutical formulation without human interference; (v) shorter manufacturing times; and (vi) batch to batch consistency.

DEFINITIONS

The following terms shall have, for the purposes of this application and the claims, the meanings below. It should be understood that when reference herein is made to a general term, such as composition, excipient, etc. one skilled in the field may make appropriate selections based on the definitions below, or based in literature references in the field, belonging to common general knowledge.

The term “injectable controlled release form or depot” refers to a subcutaneous or intramuscular injectable product containing an active pharmaceutical compound which releases the active compound over a certain period of time.

The term “controlled release dosage form” refers to a wide range of technologies, which modify the drug pharmacokinetic profile by avoiding the immediate release of the active pharmaceutical ingredient (API).

The term “vehicle” or “pharmaceutical vehicle” refers to a carrier or inactive medium used in which the pharmaceutically active agent is formulated and or administered, such as a solvent (or diluent).

The term “gellable material” refers to an ingredient, which may be an API or not, which when added to the appropriate vehicle produces a gel formulation or a viscous pharmaceutical formulation.

The term “gel formulation” refers to a pharmaceutical preparation resulting from the swelling of a substance (API or excipient) in the presence of a liquid medium. When the swelling occurs in the presence of water, the gel is referred to as hydrogel.

Additionally, it should be understood in the methods of preparation and claims herein, that the pronoun “a”, when used to refer to a reagent, such as “a base”, “a solvent” and so forth, is intended to mean “at least one” and thus, include, where suitable, single reagents as well as mixtures of reagents.

DETAILED DESCRIPTION OF THE INVENTION

Figure 1:
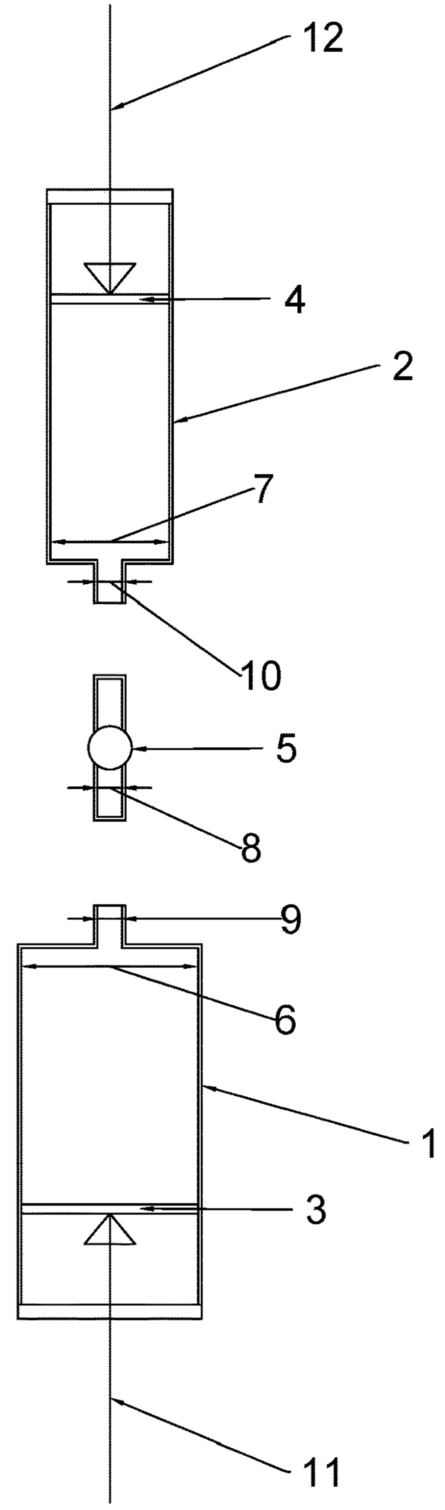
FIG. 1 illustrates an example of a two chamber apparatus according to the invention.

The present invention is directed to the preparation of viscous pharmaceutical formulations suitable for use as controlled release dosage forms. Preferred viscous pharmaceutical formulations are gels, more preferably hydrogels and even more preferably are biodegradable hydrogels.

The process for the manufacturing of a viscous pharmaceutical formulation is performed in a two chamber apparatus, in which a first (1), (21), (31) and a second chamber (2), (22), (32) are connected via a multi connector element (5), (20), (25), (35) and comprises the steps of:

a) loading a gellable material into the first chamber (1), (21), (31);
b) loading a vehicle into the second chamber (2), (22), (32);
c) transferring the vehicle from the second chamber (2), (22), (32) to the first chamber (1), (21), (31);
d) allowing the combined contents to reside in the first chamber (1), (21), (31) for a period of time;
e) transferring the combined contents from the first chamber (1), (21), (31) to the second chamber (2), (22), (32);

f) transferring the combined contents from the second chamber (2), (22), (32) to the first chamber (1), (21), (31);

g) repeating steps e) and f) until homogenized;

wherein the ratio of the internal chamber diameter CD1 (6), (26), (36) of the first chamber (1), (21), (31) to the internal chamber diameter CD2 (7), (27), (37) of the second chamber (2), (22), (32) is greater than 1.

More particularly, the process for the manufacturing of a viscous pharmaceutical formulation is performed in a two chamber apparatus in which a first (1), (21), (31) and a second chamber (2), (22), (32) are connected via a multi connector element (5), (20), (25), (35) and comprises the steps of:

a) loading a gellable material in a first chamber (1), (21), (31) with internal chamber diameter CD1 (6), (26), (36) and internal outlet diameter OD1 (9), (29), (39), b) loading a vehicle in a second chamber (2), (22), (32) with internal chamber diameter CD2 (7), (27), (37), internal outlet diameter OD2 (10), (30), (40), c) transferring the vehicle from the second chamber (2), (22), (32) to the first chamber (1), (21), (31) through a multi-connector element (5), (20), (25), (35) with internal diameter MDC (8), (28), (38) which connects the first chamber (1), (21), (31) with the second chamber (2), (22), (32), d) allowing the combined contents to reside in the first chamber (1), (21), (31) for a period of time, e) transferring the combined contents from the first chamber (1), (21), (31) to the second chamber (2), (22), (32), f) transferring the combined contents from the second chamber (2), (22), (32) to the first chamber (1), (21), (31), g) repeating steps e and f until homogenization is achieved, wherein the internal chamber diameter CD1 (6), (26), (36) is always greater than the internal chamber diameter CD2 (7), (27), (37), the internal outlet diameter OD1 (9), (29), (39) and the internal outlet diameter OD2 (10), (30), (40) are both equal to the internal diameter MCD (8), (28), (38) of the multi-connector element (5), (20), (25), (35), the ratio R1 of the internal diameter MCD (8), (28), (38) of the multi-connector element (5), (20), (25), (35) to the internal chamber diameter CD1 (6), (26), (36) of the first chamber (1), (21), (31) ranges between 0.10 and 0.35, the ratio R2 of the internal diameter MCD (8), (28), (38) of the multi-connector element (5), (20), (25), (35) to the internal chamber diameter CD2 (7), (27), (37) of the second chamber (2), (22), (32 (ranges between 0.15 and 0.50, and R1 is never equal to R2.

The apparatus may optionally comprise other elements such as valves, components and sensors that are provided for the automation of the process. Other optional elements may be an electrical cabinet, an operator panel (HMI), one or more pumps and a high precision balance.

The gellable material employed in the process may comprise an inactive ingredient, such as one or more pharmaceutical excipients with gelling properties, or one or more active pharmaceutical ingredients (API) with gelling properties, or a mixture thereof. In a preferred embodiment, the gellable material is one or more pharmaceutical excipients with gelling properties. In another preferred embodiment, the gellable material is one or more active pharmaceutical ingredients with gelling properties.

Gels are composed of two interpenetrating systems comprising colloidal particles, also known as the gelator or gellant, which are uniformly distributed throughout a dispersion medium or solvent forming a three-dimensional matrix known as the gel. The gels are prepared by adding a gellable agent (gelator) which could be natural, synthetic, or semi-synthetic polymer or low molecular weight small molecules, into a liquid such as an organic, inorganic, or aqueous solvent or mixed solvent systems. Where water is present in the liquid the gel is referred to as a hydrogel.

Examples of pharmaceutical ingredients with gelling properties are agar, carrageenan and xanthan gum, guar gum (a polymerized disaccharide of mannose and galactose), tragacanth, pectin, starch, carbomer, sodium alginate, gelatin, cellulose derivatives, polyvinyl alcohol clays, aliginate, carrageenan, carboxymethy cellulose, sodium pectate. Additionally the following polymers are mainly used for the injectable in situ formulations: Aliphatic polyesters such as poly (lactic acid), poly (glycolic acid), poly (lactide-co-glycolide), poly (decalactone) and poly ε-caprolactone. Various other polymers like methyl cellulose and hydroxypropylmethyl cellulose as well as triblock polymer systems composed of poly(D,L-lactide)-block-poly(ethylene glycol)-block-poly(DL-lactide), blends of low molecular weight poly(D,L-lactide) and poly(ε-caprolactone) are also in use. Mixtures of poly (ethylene glycol) (PEG) and poly (methacrylic acid) (PMA) as well as polymers based on poly (acrylic acid) (PAA) (carbomer, Carbopol) or its derivatives also has been used as a pH sensitive system to attain gelation. (Sanjana N K. et al./Asian Journal of Research in Biological and Pharmaceutical Sciences. 4(4), 2016, 133-142.)

Lanreotide acetate is an example of an API with inherent gelling properties. Lanreotide acetate is a synthetic cyclic octapeptide analog of the natural hormone somatostatin, chemically known as cyclo [S-S]-3-(2-naphthyl)-Dalanyl-L-cysteinyl-L-tyrosyl-D-tryptophyl-L-lysyl-L-valyl-L-cysteinyl-L threoninamide, acetate salt. The chemical structure of Lanreotide acetate is shown below:

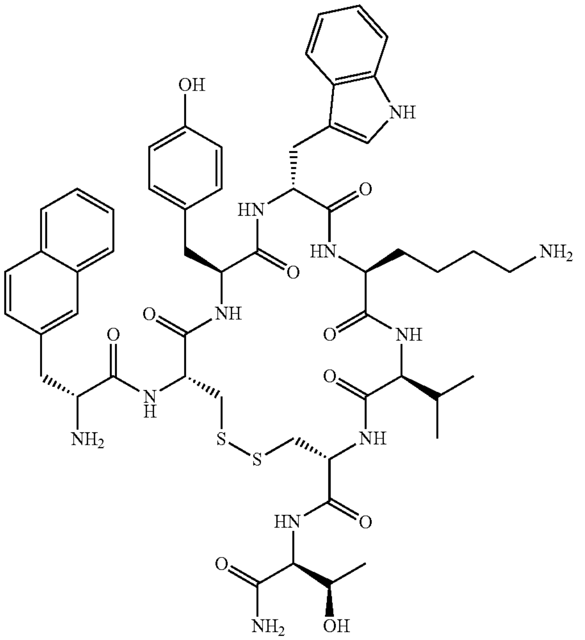 [SMILES: CC(C)[C@@H]1NC(=O)[C@H](CCCCN)NC(=O)[C@@H](Cc2c[nH]c3ccccc23)NC(=O)[C@H](Cc2ccc(O)cc2)NC(=O)[C@@H](NC(=O)[C@H](N)Cc2ccc3ccccc3c2)CSSC[C@@H](C(=O)N[C@H](C(N)=O)[C@@H](C)O)NC1=O]

Lanreotide is indicated for the treatment of acromegaly, as palliative therapy for certain types of tumors and for carcinoid syndrome on adults. The product is administered every 4 weeks in the form of a semi-solid product having a gel-like appearance.

In the case of Lanreotide, the hydrogel formulation is based on the property of it to spontaneously self-assemble into nanotubes in water (Valery et al, Biophysical Journal 2004, 86, 2484), forming a hydrogel with controlled release properties which may be injected subcutaneously to a patient. A possible mechanism suggests that the formulation forms a drug depot at the injection site due to the interaction of the formulation with physiological fluids. Drug release can occur by various mechanisms including diffusion, dissolution, passive diffusion of the drug from the depot towards the surrounding tissues, followed by the absorption into the bloodstream. The mechanism of action of Lanreotide is believed to be similar to that of natural somatostatin.

The process of the present invention may be used for the manufacturing of viscous pharmaceutical formulations with other APIs as well, which exhibit gelling properties as defined above. The API may preferably be a peptide, more preferably a somatostatin analogue, even more preferably Lanreotide or pharmaceutically acceptable salt thereof. The acetate salt is still more preferable.

The process of the present invention may also be used for the manufacturing of viscous pharmaceutical formulations with APIs which do not exhibit gelling properties. In this case, a pharmaceutical excipient with gelling properties may be comprised in the gellable material together with the non-gellable API, or, alternatively, the non-gellable API may be comprised in the vehicle.

Viscosity is a physical property affecting several other properties, in the case of pharmaceutical products, for example, injectability. A formulation with high viscosity results to an increase in injectability values, i.e. the injection force is increased as viscosity increases. Release rate can be measured by conducting in vitro release tests to determine the percentage of the active pharmaceutical ingredient released over time; an increase of the pH leads to a decrease in the release profile (dissolution rate) of the formulation. In the Lanreotide formulation the pH is directly proportional to the concentration of the acetic acid and the optimum acetic acid concentration is defined and calculated from the optimum pH range, as exemplified in EP2523653.

Injectability is a key product performance parameter for any parenteral dosage form, such as injectable emulsions, suspensions, liposomes, micro emulsions, gels and microspheres and refers to the ease of an injectable therapeutic to be administered through a needle. It is considered a critical property for efficacy, safety and patient acceptance, i.e. ease of use and patient compliance. It is also a surrogate of the viscosity of a product. The injectability allows one to draw conclusion on the evenness of flow, and freedom from clogging of the syringe. In general, it affects the performance of the delivery system.

Injectability is defined by measuring the pressure or force required for injection.

The process and the apparatus shall be described in detail with reference to the figures.

The two chambers (1), (2), (21), (31), (22), (32) comprise of a main body wherein the internal chamber diameters (6) (26), (36), (7), (27), (37) can be found and a chamber outlet part wherein the internal outlet diameters (9), (29), (39), (10), (30), (40) can be found.

Figure 4:
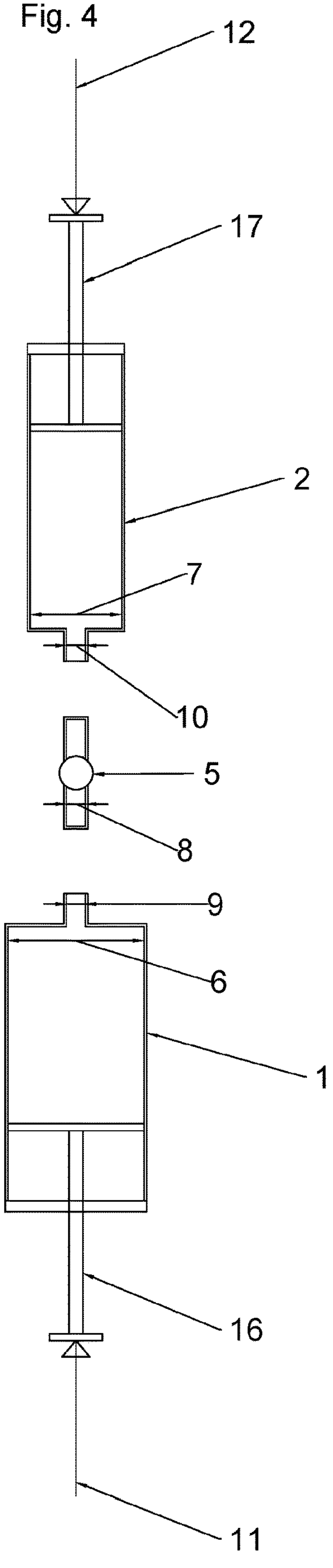
FIG. 4 illustrates another preferred embodiment of the invention, wherein the means for applying pressure are pistons.
Figure 5:
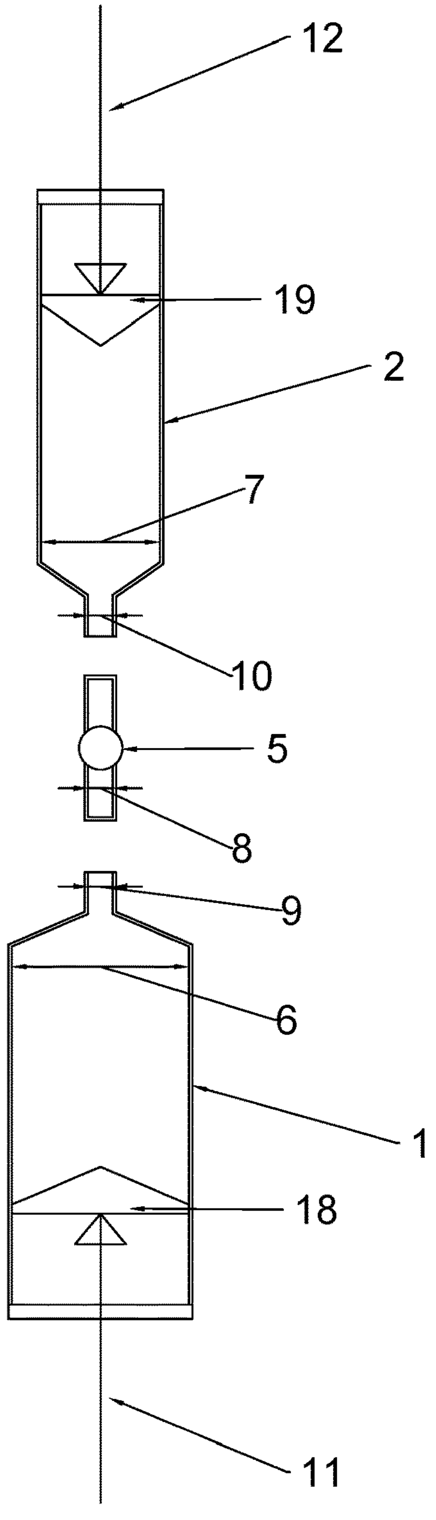
FIG. 5 illustrates another preferred embodiment of the invention, wherein the means for applying pressure have conical shape.
Figure 6:
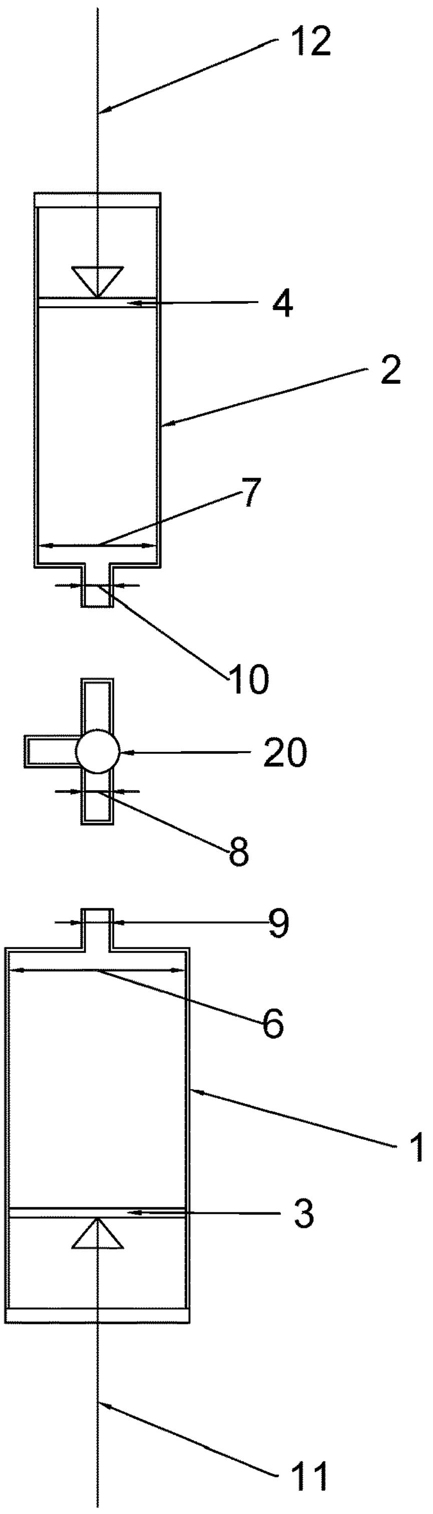
FIG. 6 illustrates another preferred embodiment of the invention, wherein the multi connector element is a three-way connection.
Figure 7:
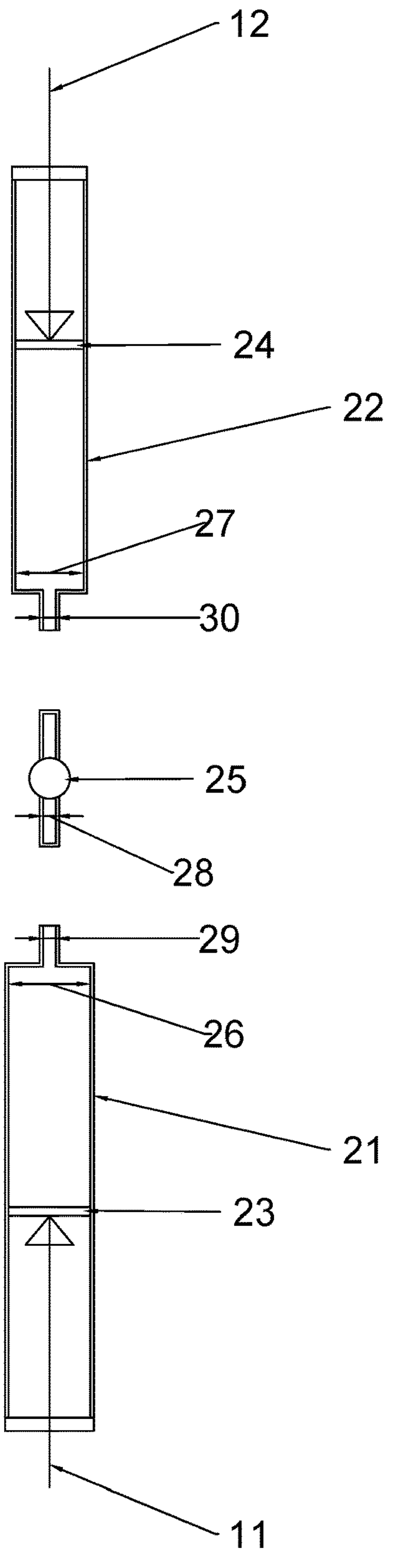
FIG. 7 illustrates another preferred embodiment of the invention, with different dimensions than FIG. 1.
Figure 8:
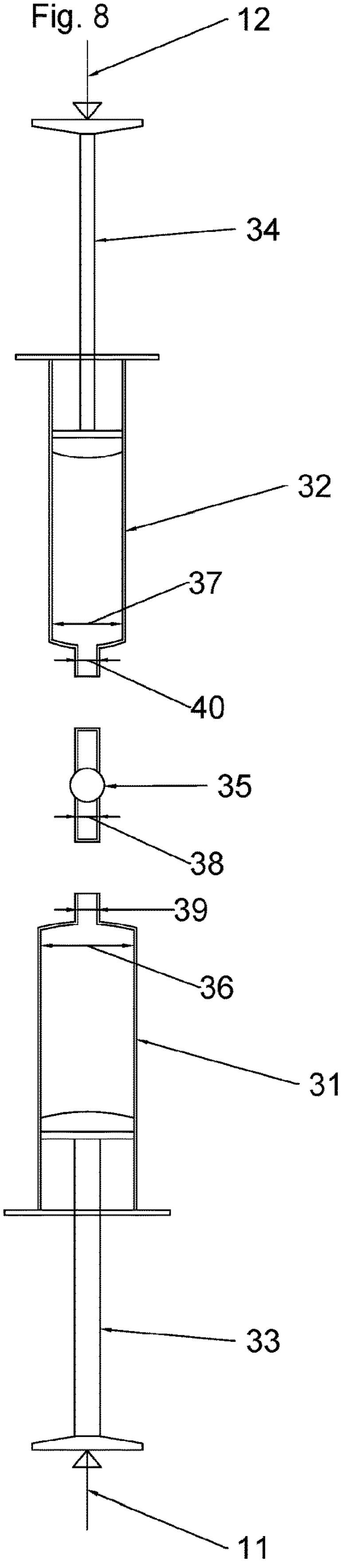
FIG. 8 illustrates another preferred embodiment of the invention, wherein the chambers are syringes.
Figure 9:
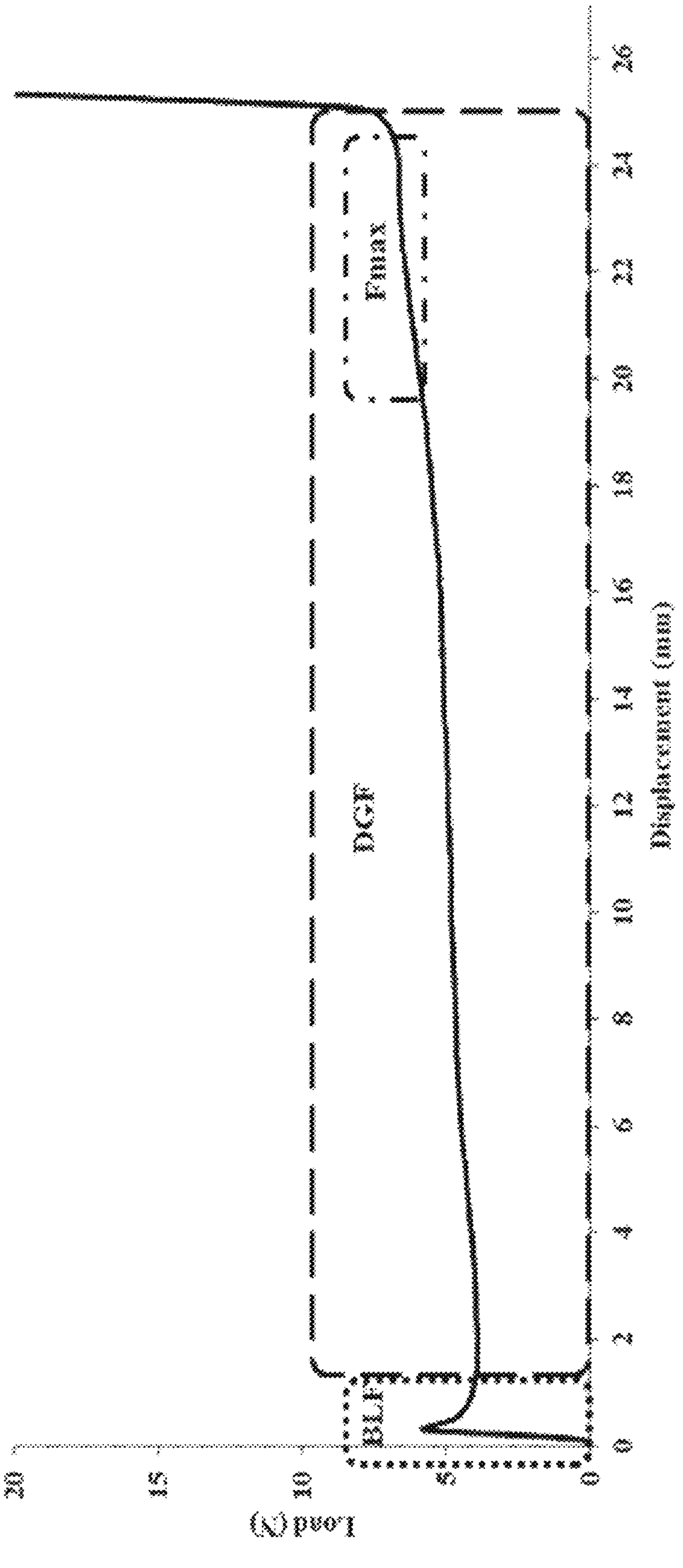
FIG. 9 illustrates a typical injectability measurement combining the dot-lined area that denotes the Break Loose Force (BLF), the dot and broken-line area where the Maximum Force (Fmax) is observed and the broken-line area that denotes the Dynamic Gliding Force (DGF) area.

In an embodiment the chambers may be equipped with a means for applying pressure (3), (4), (16), (17), (18), (19), (23), (24), (33), (34). The means for applying pressure has a shape complementary to the internal shape of the chamber outlet part, configured to expel all the material upon movement of the means for applying pressure towards the chamber outlet part. This ensures minimum loss of the contents. The means for applying pressure may be circular elements (3), (4) in the case of cylindrical chambers, wherein a force is applied (11), (12) (FIGS. 1, 2, 3, 6, 7) to or via pistons (16), (17) (FIG. 4), conical elements (18), (19) (FIG. 5) or plungers (33), (34) (FIG. 8).

The two chambers are connected via a multi-connector element (5), (20), (25), (35) along their longitudinal axis. Pressure in the form of an external force (11), (12) is applied to transfer the content of its chamber to the other chamber, by means of a reciprocating movement. This may be provided, for example, by a pneumatic system using compressed air. Other means for inducing reciprocating movement may be a hydraulic or electric pump acting on a piston. A vacuum pump is also used as an auxiliary equipment to assist the compression of the gellable material in order to remove trapped air or other gas to bring it to the desired volume, when this is required. The vacuum pump, not shown in the Figures, may be connected with the apparatus via the multi-connector element (5), (20), (25), (35).

This basic setup of the apparatus is also exemplified in International Patent Publication WO 96/07398.

The chamber may be any kind of vessel compatible with the contents it is intended to hold and that can withstand the forces developed during the process exercised on it. It may be for example a vessel, as depicted in FIG. 1-7 or a syringe, depicted in FIG. 8. In a preferred embodiment one or both of the chambers are cylindrical. In another preferred embodiment the chambers are made of metal and more preferably from stainless steel. Each chamber is characterized by an internal chamber diameter (6), (7), (26), (27), (36), (37) and an internal outlet diameter (9), (10), (29), (30), (39), (40). The internal chamber diameters may vary with respect to each chamber. The internal outlet diameters of each chamber are equal.

The chambers are designed and equipped appropriately so as to allow charging of the components into them, i.e. the gelling material and the vehicle (not shown in the Figures).

The size of the chamber is not a critical feature. When using syringes as chambers, the length can be as small as a syringe can be. Otherwise the size of the chamber can be adjusted according to the batch size of the mixture to be produced. It may be from a few centimeters (5 cm) to as long as a meter. The chamber should not be too narrow or too wide when taking into account the ratio of the internal chamber diameter and the respective length. The ratio of the length to the respective internal chamber diameter may be from 1 to 10, more preferably from 2 to 10 and most preferably from 4 to 8.

The multi-connector element (5), (20), (25), (35) controls the passage of the gellable material and/or fluid and/or air from the outlet of the first or second chamber. The multi-connector element (5), (20), (25), (35) may for example be a valve, preferably a three-way valve which has the additional advantage of serving as an outlet of the mixture after its homogenization. The dimensions of it, particularly its inner diameter MCD (8), (28), (38) are adjusted to match the dimensions of internal outlet diameters of the first (9), (29), (39) and second chamber (10), (30), (40) and thus is implicitly defined by them. The multi-connector element (5), (20), (25), (35) can isolate the chambers by appropriate adjustments. For example, in the case of a valve, this is provided by switching it to its side position.

The whole assembly must be such that it can provide a tight sealed system with minimum headspace, to minimize losses and allow for the application of vacuum, if required.

Furthermore, the manner in which parts of the assembly are movable is not important, in order for the reciprocating movement of the means for applying pressure (3), (4), (16), (17), (18), (19), (23), (24), (33), (34) to occur. In reference to an external system, it may be that the means for applying pressure (3), (4), (16), (17), (18), (19), (23), (24), (33), (34) are movable or that the rest of the apparatus is movable. In any case, the relative movement of the means for applying pressure (3), (4), (16), (17), (18), (19), (23), (24), (33), (34) to the rest of the apparatus is such that it provides a reciprocating movement thereby moving the contents of one chamber into the other chamber.

Figure 2:
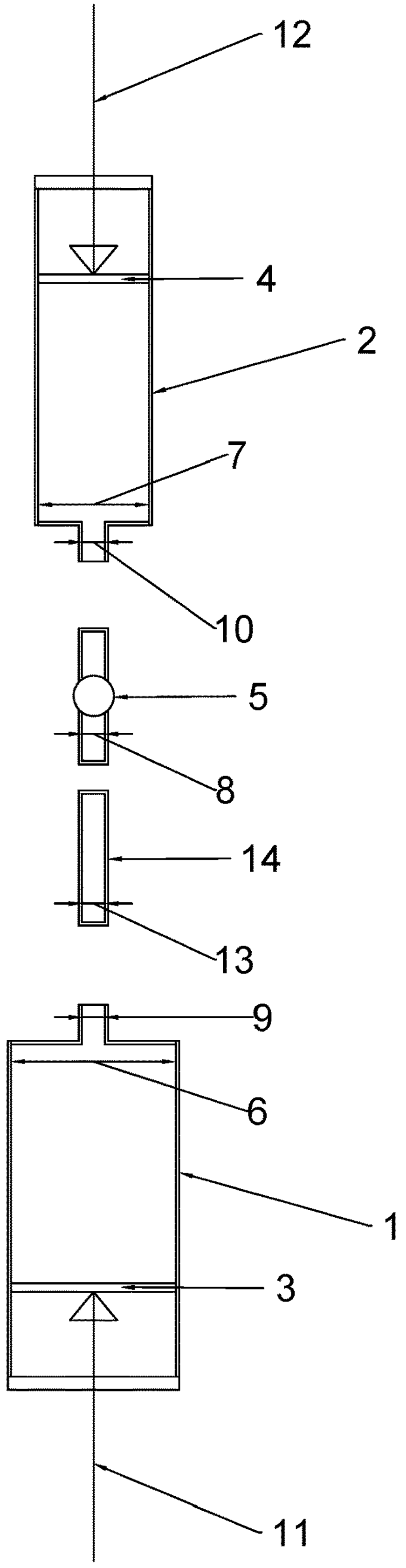
FIG. 2 illustrates a preferred embodiment of the invention, with an extension tube.
Figure 3:
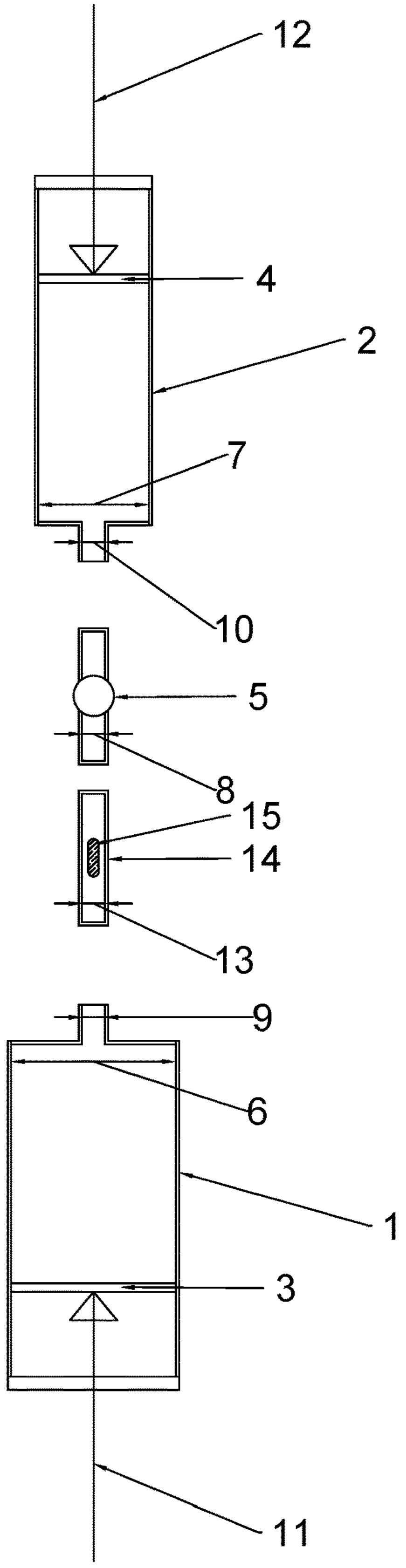
FIG. 3 illustrates another preferred embodiment of the invention, wherein the extension tube is partially made of glass.

In a preferred embodiment, the apparatus further comprises an extension tube (14) as shown in FIGS. 2 and 3. The extension tube is suitable for transferring the contents of the chambers from the first (1), (21), (31) to the second chamber (2), (22), (32) and vice versa. It may comprise a static mixer in its inner part. In a more preferred embodiment, the extension tube (14) is at least partially made of glass (15) as shown in FIG. 3, which allows for optical in-process control of the homogenization. The extension tube has an internal diameter (13) equal to the internal diameter MCD (8), (28), (38) of the multi-connector element (5), (20), (25), (35) and the internal chamber outlet diameters OD1 (9), (29), (39) and OD2 (10), (30), (40) of the first (1), (21), (31) and second chamber (2), (22), (32). The extension tube may be either connected with the first chamber (1), (21), (31) and the multi-connector element (5), (20), (25), (35) or with the multi-connector element (5), (20), (25), (35) and the second chamber (2), (22), (32).

The gellable material is provided in powder form and transferred into the first chamber (1), (21), (31) of the apparatus. The other end of the first chamber (1), (21), (31) is connected with the multi-connector element (5), (20), (25), (35).

In certain formulations the final volume of the gellable material in the chamber is a critical parameter that may significantly affect the next steps of manufacturing. For example, in the case of Lanreotide, it has been shown that, after packing, the API gellable material mass should have a final volume in the chamber, before adding the vehicle, that is equal or approximately equal to the quantity of vehicle to be added. This allows the addition of a vehicle into the total mass of the gellable material resulting into the initial formation of a semi-solid material that is subjectable to homogenization.

In a preferred embodiment, once the gellable material is introduced and isolated into the first chamber (1), (21), (31) its capacity is adjusted to a volume approximating or equal to the volume occupied by the vehicle to be added, by applying pressure (3), (16), (18), (23), (33). The isolation of the first chamber prevents air from being introduced into the system. In a more preferred embodiment, vacuum may be applied to aid the volume adjustment by removing trapped gas or air, depending on the bulk density of the gellable material. Lower bulk densities, resulting from higher specific surface areas, may require the additional assistance of vacuum for proper packing of the material. A filtration sieve and an extension with the pressure gauge may further be connected to the multi-connector element (5), (20), (25), (35) and attached to the vacuum pump. This prevents suction of the gellable material into the vacuum pump.

An appropriate amount of vehicle is introduced into the second chamber (2), (22), (32). The vehicle may be water, including water for injection or any other aqueous medium, an organic solvent with or without water, an anhydrous liquid or an injectable oil. Examples of substances which can be used as vehicles, or more particularly as solvents, in the present invention, are disclosed in EP2823808 which is incorporated herein by reference. The vehicle may further comprise one or more pharmaceutical excipients which serve as components of the final formulation.

The first (1), (21), (31) and second chamber (2), (22), (32) are connected by means of adjusting the multi-connector element (5), (20), (25), (35) to a position where the vehicle can be transferred from the second chamber (2), (22), (32) to the first chamber (1), (21), (31) through the multi-connector element (5), (20), (25), (35). This transfer from one chamber to the other is preferably brought about by the reciprocating movement of the means for applying pressure (3), (4), (16), (17), (18), (19), (23), (24), (33), (34).

When transferring is completed, the first chamber is isolated again by means of adjusting the multi-connector element (5), (20), (25), (35) in the proper position and an amount of time is given to allow the combined contents to reside in the first chamber.

In a preferred embodiment, a sufficient amount of time is provided for the vehicle and the gellable material to interact. In an even more preferred embodiment, a sufficient amount of time is provided for the vehicle to hydrate the gellable material. A sufficient amount of time may be from a few minutes to several hours, preferable from 10 minutes to 3 hours, more preferable from 15 minutes to 2 hours, even more preferably from 30 to 60 minutes.

Into the next step, the first chamber (1), (21), (31) is connected again to the second chamber (2), (22), (32) and the homogenization procedure is initiated. The combined contents are transferred from the first chamber (1), (21), (31) to the second chamber (2), (22), (32) followed by transfer of the hydrated mixture from the second chamber (2), (22), (32) to the first chamber (1), (21), (31). The combined contents continue to be transferred from the first chamber (1), (21), (31) to the second chamber (2), (22), (32) and vice versa through the multi-connector element (5), (20), (25), (35) until the mixture is homogenized.

In an embodiment, transferring the contents from the first chamber to the second chamber and vice versa is performed by means of a reciprocating movement of the means for applying pressure (3), (4), (16), (17), (23), (24), (33), (34).

During the homogenization process Fmax and Faverage were measured. The Maximum Force (Fmax) is the highest force measured from the point where the injection force profile starts reaching a plateau (displacement vs Force) and until the plunger finishes its course at the front end of the syringe or container (before the rapid force increase exhibited due to the compression of the plunger against the end of the syringe). The Dynamic Glide Force (DGF or Faverage) is calculated as the average force in the plateau region of the data which corresponds to the displacement ranges appropriate for different syringes.

A typical injectability test measures the force required for the displacement of the syringe plunger for the content of the syringe to be extracted through the needle. The profile exhibits an initial sharp increase in the force required during the first millimeters of displacement, followed by a stabilization area (plateau area). The plateau is observed until a final rapid increase in the applied force, corresponding to the point where the plunger finishes its course at the front end of the syringe (i.e. after the extraction of the syringe contents is completed). To evaluate a drug apparatus and furthermore a drug formulation through injectability measurements, three different parameters are examined. The Break Loose Force (BLF), the Maximum Force (Fmax) and the Dynamic Glide Force (DGF).

The first parameter is the Break Loose Force (BLF) and is observed during the first millimeters of plunger displacement. BLF corresponds to the maximum force required to bypass the adhesion forces developed between the inner syringe barrel and the rubber stopper. Studying the BLF is useful for stability purposes where the interactions of the rubber stopper with the drug formulation can alter the level of the initial force needed to start the administration.

The most valuable factor is the Dynamic Gliding Force (DGF) and is defined as the average force calculated in the plateau area. This corresponds to the force required to maintain uninterrupted transfer of the contents at a stable displacement rate. This is the most critical measurement for the evaluation of the apparatus mainly because it relates to the easiness of the administration to a patient. Comparing the DGF between different formulations, information about the viscosity, concentration and other characteristics can be identified. Finally, the Maximum Force (Fmax) is defined as the maximum observed force in the plateau area during injectability measurement. This factor can present information about the homogeneity of the sample, possible clogging etc., when combined with Dynamic Gliding Force (DGF).

The inventors have unexpectedly discovered that the homogeneity of a viscous pharmaceutical formulation can be influenced by the specific dimensions of the chambers. Particularly, the internal chamber diameters CD1 (6), (26), (36) and CD2 (7), (27), (37), the outlet diameters OD1 (9), (29), (39) and OD2 (10), (30), (40) and their respective ratios were found to play an important role to the homogenization process. Because the internal outlet diameter OD1 (9), (29), (39) and the internal outlet diameter OD2 (10), (30), (40) are both equal to the internal diameter MCD (8), (28), (38) of the multi-connector element (5), (20), (25), (35), it is more simple to generally refer to the internal diameter MCD (8), (28), (38)., For defining the optimum dimensions, the bulk gel produced by the process of the invention was subjected to injectability tests and viscosity tests, by withdrawing samples from different parts of it. Sufficient homogeneity was considered to have been achieved when the deviation between the analytical results of different samples was not significant (see Table 1).

Optimum results are obtained when the ratio R1 of the MCD (8), (28), (38) of the multi-connector element (5), (20), (25), (35) to the CD1 (6), (26), (36) of the first chamber (1), (21), (31) is between 0.10-0.35 and the ratio R2 of the MCD (8), (28), (38) of the multi-connector element (5), (20), (25), (35) to the CD2 (7), (27), (37) of the second chamber (2), (19) is between 0.15-0.50. In addition, the internal chamber diameter CD1 (6), (26), (36) is always greater than the internal chamber diameter CD2 (7), (27), (37), and R1 should never be equal to R2.

The inventors believe that the above parameters are critical and define the physical characteristics of the final gel formulation that in turn affect the degradation rate and consequently the release characteristics of the prepared formulation. The proposed diameter ratios allow the homogenization procedure to be completed at about 2-3 hours, during which about 60 transferring cycles are made, i.e. from the first to the second chamber and vice versa, although, manufacturing times up to 15 hours may be required for satisfactory homogenization.

EXAMPLES 66.8 g of Lanreotide API with peptide content 92.0% and acetate content 5.5% are introduced into the first chamber (1) and packed using a vacuum pump until a volume of 174.31 mL. 216.08 g of WFI (water for injection) are mixed with 3.69 g of acetic acid until a clear colorless solution is achieved. 193.02 g of this solution are charged to the second chamber. After the packing of the API, 193.02 g of the aqueous acetic acid solution are transferred in the first chamber. Sufficient time is allowed for the API to be hydrated appropriately (i.e., 60 min). Once this is achieved both chambers are connected, and the homogenization procedure starts by passing the hydrated mixture from the first to the second chamber and vice versa. The homogenization proceeds till the hydrated mixture is considered fully homogenized.

The bulk product homogeneity was assessed by % RSD (Relative Standard Deviation) assay in terms of Injectability from three different parts of the bulk product. A low % RSD signifies that the product is more homogeneous.

Injectability

The gel product is filled into syringes and the force vs displacement data as well as the plot are exported from the measurement using a Shimadzu EZ-SX Texture Analyzer.

Viscosity

Rheological sample characterization was performed by dynamic oscillatory measurements as a function of strain and angular frequency (namely, strain and frequency sweep test), using an AR-G2 controlled stress rheometer from TA Instruments.

TABLE 1

| | Diameter Ratios | | Injectability | | Viscosity | | | |
|---|---|---|---|---|---|---|---|---|
| Example | R1 | R2 | Faverage RSD (%) | Fmax RSD (%) | G' (Pa) | G' RSD (%) | G"(Pa) | G"RSD (%) |
| 1 | 0.24 | 0.24 | 7.0 | 6.5 | 284,300 | 59.8 | 44,800 | 54.5 |
| 2 | 0.08 | 0.08 | 6.6 | 6.9 | 420,500 | 43.2 | 60,100 | 48.6 |
| 3 | 0.09 | 0.11 | 9.9 | 10.0 | 384,100 | 41.5 | 53,830 | 40.1 |
| 4 | 0.12 | 0.13 | 10.5 | 9.9 | 321,700 | 34.5 | 46,530 | 36.8 |
| 5 | 0.16 | 0.19 | 1.0 | 1.1 | 258,400 | 18.0 | 39,900 | 18.9 |
| 6 | 0.17 | 0.20 | 1.5 | 2.2 | 251,300 | 17.8 | 38,730 | 18.4 |

TABLE 1-continued

| | Diameter | | Injectability | | Viscosity | | | |
|---|---|---|---|---|---|---|---|---|
| | Ratios | | Faverage | Fmax RSD | | G' RSD | | G"RSD |
| Example | R1 | R2 | RSD (%) | (%) | G' (Pa) | (%) | G"(Pa) | (%) |
| 7 | 0.23 | 0.27 | 1.4 | 1.7 | 242,400 | 18.4 | 38,451 | 19.1 |
| 8 | 0.47 | 0.53 | 3.3 | 4.3 | 79,900 | 65.0 | 10,020 | 68.1 |

Examples 1 and 2: When R1 is equal to R2 the process lasts for too many hours for homogenization and the results obtained are not acceptable.

Examples 3 and 4: When one or both of the ratios R1, R2 take values lower than 0.10 and 0.15 respectively, this results in poor homogeneity of the samples and long hours of production.

Examples 5,6 and 7: When both ratios R1, R2 take values within the ranges 0.10-0.35 and 0.15-0.50 respectively a gel with good homogeneity is produced within 2-3 hours.

Example 8: When ratios R1, R2 take values higher than 0.35 and 0. 05 respectively this results in a non-homogeneous product.

The invention claimed is:

1. A process for manufacturing a viscous pharmaceutical formulation in a two chamber apparatus in which a first and a second chamber are connected via a multi connector element, the process comprising:

(a) loading a gellable material into the first chamber;

(b) loading a vehicle into the second chamber;

(c) transferring the vehicle from the second chamber to the first chamber, to obtain combined contents;

(d) allowing the combined contents to reside in the first chamber for a period of time;

(e) transferring the combined contents from the first chamber to the second chamber;

(f) transferring the combined contents from the second chamber to the first chamber; and (g) repeating the transferring (e) and the transferring (f) until the combined contents are homogenized, wherein a CD1/CD2 ratio of a first internal chamber diameter CD1 of the first chamber to a second internal chamber diameter CD2 of the second chamber is in a range of from 1.08 to 1.5.

2. The process of claim 1, wherein, in the allowing (d), a sufficient amount of time is provided for the vehicle and the gellable material to interact.

3. The process of claim 1, wherein the first chamber comprises a first pressure applicator and the second chamber comprises a second pressure applicator, and wherein the transferring of the combined contents from the first chamber to the second chamber and vice versa is performed by a reciprocating movement of the first and/or second pressure applicator.

4. The process of claim 3, wherein the first and/or second pressure applicator is a piston or a plunger.

5. The process of claim 1, wherein after the loading (b) and prior to proceeding to the transferring (c), the first chamber's capacity is adjusted to a volume approximating or equal to the volume occupied by the vehicle, by pressure of a first pressure applicator.

6. The process of claim 5, wherein the adjustment of the first chamber capacity is assisted by the application of vacuum.

7. The process of claim 6, wherein vacuum is applied through a filtration sieve.

8. The process of claim 1, wherein the first chamber and/or the second chamber is cylindrical.

9. The process of claim 1, wherein the multi-connector element is a valve.

10. The process of claim 9, wherein the valve is a three-way valve.

11. The process of claim 1, further comprising:

an extension tube, connected to the multi-connector element and the first chamber or to the multi-connector element and the second chamber.

12. The process of claim 11, wherein the extension tube is at least partially made of glass.

13. The process of claim 1, wherein the gellable material comprises an active pharmaceutical ingredient with one or more gelling properties, and/or a pharmaceutical excipient with one or more gelling properties.

14. The process of claim 1, wherein the vehicle comprises a pharmaceutical excipient and/or an active pharmaceutical ingredient, with no gelling properties.

15. The process of claim 1, wherein the gellable material is Lanreotide or a pharmaceutically acceptable salt thereof.

16. A two-chamber apparatus configured for implementing the process of claim 1, the apparatus comprising:

(a) the first chamber configured for holding the gellable material;

(b) the second chamber configured for holding the vehicle; and (c) the multi-connector element suitable for controlling passage of the gellable material, the vehicle, air, or a mixture thereof, from an outlet of the first or second chamber, wherein the multi-connector element connects the first chamber with the second chamber.

17. The apparatus of claim 16, wherein the first chamber comprises a first pressure applicator, and wherein the second chamber comprises a second pressure applicator.

18. The apparatus of claim 17, wherein the first and/or second pressure applicator is a piston or a plunger.

19. The apparatus of claim 16, wherein the first and/or second chamber is cylindrical.

20. The apparatus of claim 16, wherein the multi-connector element is a valve.

21. The apparatus of claim 20, wherein the valve is a three-way valve.

22. The apparatus of claim 16, further comprising:

a vacuum applicator configured to apply a vacuum to the first chamber.

23. The apparatus of claim 22, further comprising:

a filtration sieve.

24. A two chamber apparatus configured for implementing the process of claim 1, the apparatus comprising:

(a) the first chamber with the first internal chamber diameter CD1 and a first internal outlet diameter OD1, configured for holding the gellable material;

(b) the second chamber with the second internal chamber diameter CD2 and a second internal outlet diameter OD2, configured for holding a vehicle; and (c) the multi-connector element with the with a multi-connector internal diameter MCD, configured for controlling passage of the gellable material, the vehicle, air, or a mixture thereof, from an outlet of the first or second chamber, which connects the first chamber with the second chamber, wherein the first internal chamber diameter CD1 is always greater than the second internal chamber diameter CD2, wherein a ratio R1 of the multi-connector internal diameter MCD to the first internal chamber diameter CD1 is in a range of from 0.10 to 0.35, wherein a ratio R2 of the multi-connector internal diameter MCD to the second internal chamber diameter CD2 is in a range of from 0.15 to 0.50, and wherein the ratio R1 is never equal to the ratio R2.

25. The apparatus of claim 16, further comprising:

an extension tube with an internal diameter TD equal to the multi-connector internal diameter MCD, connected to the multi-connector element and the first chamber or to the multiconnector element and the second chamber.

26. The apparatus of claim 25, wherein the extension tube is at least partially made of glass.

27. A product, obtained by the process of claim 1.

28. A process for manufacturing a viscous pharmaceutical formulation in a two chamber apparatus in which a first and a second chamber are connected via a multi connector element, the process comprising:

(a) loading a gellable material in the first chamber with a first internal chamber diameter CD1 and a first internal outlet diameter OD1;

(b) loading a vehicle in the second chamber with a second internal chamber diameter CD2 and a second internal outlet diameter OD2;

(c) transferring the vehicle from the second chamber to the first chamber through the multi-connector element with a multi-connector internal diameter MCD;

(d) allowing combined contents to reside in the first chamber for a period of time;

(e) transferring the combined contents from the first chamber to the second chamber;

(f) transferring the combined contents from the second chamber to the first chamber; and (g) repeating the transferring (e) and the transferring (f) until the combined contents are homogenized, wherein the first internal chamber diameter CD1 is always greater than the second internal chamber diameter CD2, wherein the first internal outlet diameter OD1 and the second internal outlet diameter OD2 are both equal to the multi-connector internal diameter MCD, wherein a ratio R1 of the multi-connector internal diameter MCD to the first internal chamber diameter CD1 is in a range of from 0.10 to 0.35, wherein a ratio R2 of the multi-connector internal diameter MCD to the second internal chamber diameter CD2 is in a range of from 0.15 to 0.50, and wherein the ratio R1 is never equal to the ratio R2.

* * * * *